(12) United States Patent
Nilsson Neijber

(10) Patent No.: US 9,764,010 B2
(45) Date of Patent: Sep. 19, 2017

(54) METHOD FOR TREATING PREMATURE EJACULATION WITH A NEUROTOXIN

(71) Applicant: Allergan, Inc., Irvine, CA (US)

(72) Inventor: Anders N. Nilsson Neijber, Malmo (SE)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/971,542

(22) Filed: Aug. 20, 2013

(65) Prior Publication Data
US 2014/0065130 A1 Mar. 6, 2014

Related U.S. Application Data

(60) Provisional application No. 61/693,192, filed on Aug. 24, 2012.

(51) Int. Cl.
*A61K 38/48* (2006.01)
*A61K 39/08* (2006.01)

(52) U.S. Cl.
CPC ................................. *A61K 38/4893* (2013.01)

(58) Field of Classification Search
None
See application file for complete search history.

(56) References Cited

U.S. PATENT DOCUMENTS

| | | | |
|---|---|---|---|
| 8,361,789 B2 | 1/2013 | Zhu | |
| 8,618,261 B2 | 12/2013 | Ester | |
| 2009/0186052 A1* | 7/2009 | Cherif-Cheikh ... | A61K 38/4886 424/239.1 |
| 2011/0052636 A1 | 3/2011 | Gaxiola | |

OTHER PUBLICATIONS

Morris ("Circumcision and Anesthesia", available at www.circinfo.net/anesthesia.html, webcapture from Apr. 25, 2011curtosey of the Wayback Machine).*
Pertek ("Bloc penien chex l'adulte: Penile block in adults" Ann Fr Anesth Reanim, 11 82-87, 1992).*
The Merck Manual, 16th Edition, pp. 1576-1577, published by Merck Research Laboratories 1992.
Habermann, Ernst, et al., "Tetanus Toxin and Botulinum A and C Neurotoxins Inhibit Noradrenaline Release from Cultured Mouse Brain," J Neurochem 51(2); 522-527:1988.
Jankovic, Joseph, edited "Therapy With Botulinum Toxin," Marcel Dekker; 71-85:1994.
Schantz, Edward J., et al., "Properties and Use of Botulinum Toxin and Other Microbial Neurotoxins in Medicine," Microbiol Rev, 56; 80-99:1992.
Sloop, R. Richard, et al., "Reconstituted Botulinum Toxin Type A Does Not Lose Potency in Humans If It Is Refrozen or Refrigerated for 2 Weeks Before," Neurology, 48;249-253:1997.
The International Search Report/US2013/056088, Dec. 2, 2013.
Perretti, A., et al., "Neurophysiologic evaluation of central-preipheral sensory and motor pudendal pathways in primary premature ejaculation," Urology, vol. 61, No. 3, Mar. 1, 2003, pp. 623-628 (XP055089881).
Serefoglu, Ege Can, et al., "Botulinum toxin-A injection may be beneficial in the treatment of life-long premature ejaculation," Medical Hypotheses, vol. 74, No. 1, Jan. 1, 2010, pp. 83-84 (XP026776486).
Waldinger, Marcel D., et al. "Premature ejaculation and serotonergic antidepressants-induced delayed ejaculation: the involvement of the serotonergic system," Behavioural Brain Research, vol. 92, No. 2, May 1, 1998, pp. 111-118, (XP001197232).

* cited by examiner

*Primary Examiner* — Louise W Humphrey
*Assistant Examiner* — Charles Zoltan Constantine
(74) *Attorney, Agent, or Firm* — Brigitte C. Phan; Ted A. Chan

(57) ABSTRACT

Methods for treating premature ejaculation and prolongation of climax time in a patient in need thereof by local administration of a Clostridial neurotoxin, such as a botulinum toxin, are provided.

8 Claims, 2 Drawing Sheets

METHOD FOR TREATING PREMATURE EJACULATION WITH A NEUROTOXIN

CROSS-REFERENCES TO RELATED APPLICATIONS

This application claims the benefit of U.S. Provisional Application Ser. No. 61/693,192, filed Aug. 24, 2012, incorporated entirely by reference.

FIELD OF INVENTION

The present invention relates to methods of treating premature ejaculation with a neurotoxin such as a botulinum toxin.

BACKGROUND

Premature ejaculation is a very common sexual dysfunction in men, particularly those in the age range of about 18 to about 40 years old. It has been reported that premature ejaculation affects some 20-30% of adult men [Laumann, 2005].

Premature ejaculation may be classified as primary or secondary, in accordance with the Diagnostic and Statistical Manual of Mental Disorders, Fourth Edition (DSM-IV), which classifies sexual disorders into 4 particular categories: (1) primary, (2) general medical condition-related, (3) substance-induced, and (4) not otherwise specified. Primary applies to individuals who have had the condition since they became capable of functioning sexually (ie, postpuberty). Secondary indicates that the condition manifests itself in an individual where an acceptable level of ejaculatory control was previously had, and then began to experiencing premature ejaculation thereafter. The majority of patients with premature ejaculation have a primary premature ejaculation.

Premature ejaculation can be generally defined as the occurrence of ejaculation prior to or sooner than hoped for by one or both sexual partners [e.g. see 'The Merck Manual', 16th Edition, p 1576, published by Merck Research Laboratories, 1992]. Premature ejaculation was defined by the International Society of Sexual Medicine (ISSM) as "a male sexual dysfunction characterized by ejaculation that always or nearly always occurs prior to or within about one minute of vaginal penetration; the inability to delay ejaculation on all or nearly all vaginal penetrations; and negative personal consequences such as distress, bother, frustration, and/or avoidance of sexual intimacy" [McMahon 2008, Waldinger 2005]. The inclusion of the intravaginal ejaculatory latency time (IELT) in the ISSM definition has added an objective measurement based on normative data to the characterization of primary premature ejaculation.

Other very similar definitions of premature ejaculation exist, e.g. the Diagnostic and Statistical Manual of Mental Disorders, 4th Edition, (DSM-IV), the World Health Organization (WHO) (1993 [ICD-10]), and the American Urological Association's [AUA] guideline on the pharmacological management of PE [Colpi 2004, Montague et al 2004]. All premature ejaculation definitions include the primary concept of ejaculatory latency time that is persistent shorter than desired with minimal sexual stimulation, and the key dimensions of distress and interpersonal difficulty caused by premature ejaculation.

Premature ejaculation is reported to affect an individual's sexual function, self-esteem, and ability to participate in intimate relationships [Rowland et al 2004, Symonds et al 2003]. Men with self-reported premature ejaculation have a lower frequency of sexual intercourse, higher levels of intercourse-related anxiety and lower levels of sexual satisfaction [Pereleman 2004, Patrick 2005].

Although ejaculatory disorders were previously assumed to be psychological or secondary to a medical background, several primary neurobiological causes have been suggested. Animal and human sexual psychopharmacological studies have attributed a neurobiological basis, and possible genetic etiology, to primary premature ejaculation [Waldinger 2002].

Premature ejaculation can be experienced as ejaculation before, upon or shortly after penile penetration of a sexual partner.

Premature ejaculation can occur at virtually any age in an adult man's life. As a reported condition, it is most common in younger men (aged 18-30 years old) but may also occur in conjunction with secondary impotence in men aged 45-65 years.

There are known non-drug treatments and drug treatments for premature ejaculation. Examples of known non-drug treatments for premature ejaculation include the squeeze technique developed by Masters & Johnson (1970) and the stop-start technique developed by Semans (1956). However, limitations of the two techniques include the fact that they are time-consuming and require the proper participation of the partner, leading to difficulty in practice and low success rates.

Since the FDA has not yet approved a drug for premature ejaculation, all medical treatments in the US are classified as off-label indications. Many central and peripheral acting agents have been proposed to treat primary premature ejaculation. These include selective serotonin reuptake inhibitors (SSRIs), tricyclic antidepressants, monoamine oxidase inhibitors 4-topical anesthesies, neuroleptics, sympatholytics, and phosphodiestrase inhibitors. Only chronic SSRIs and on-demand topical anaesthetic agents have consistently revealed beneficial effects in the prescription of premature ejaculation. Dapoxetine (Priligy®) is an oral short-acting SSRI which is the only drug currently registered for the treatment of PE in Europe and other countries, but not in the US. However, the long-term use of many of these drugs (e.g. SSRIs) can for example, increase the incidence of side effects such as vomiting, dry mouth, drowsiness, reduced libido and an ejaculation. Moreover, SSRIs are intended for chronic use rather than on-demand use because they have a long half-life and a long Tmax, which is the time to maximal plasma concentration, and it takes a long time for SSRIs to exert their therapeutic effects or efficacies, and these are difficult to predict.

Another example of off-label use of a drug for treating premature ejaculation includes the application of topical anesthetics (e.g. lidocaine 5% cream, or a lidocaine-prilocalne cream) to the penis before intercourse. However drawbacks associated with the use such anesthetics include undesired short term inability of the patient to achieve an erection, decreased penile sensation and/or vaginal numbness in a female partner.

Despite the prevalence of this condition and its debilitating effects, the lack of an effective treatment with minimal side effects, combined perhaps with a sense of stigma and the perception that no effective treatment is available, has led to a significant proportion of self-reported sufferers of premature ejaculation who have never been treated.

There is a need for a new and improved method for treating premature ejaculation and/or prolongation of climax time. In particular, a long lasting, non-systemic method for treating premature ejaculation and/or prolongation of climax time is desired that does not entail oral or repeated ingestion of a pharmaceutical compound prior to engaging in sexual activity.

The genus *Clostridium* encompasses over one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, Critical Aspects of Bacterial Protein Toxins, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each. Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E. et al., Botulinum Toxin Type B: Experimental and Clinical Experience, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotypes A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kDa) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kDa. Interestingly, the botulinum toxins are released by Clostridial bacterium as complexes comprising the 150 kDa botulinum toxin protein molecule along with associated non-toxin proteins. Thus, the botulinum toxin type A complex can be produced by Clostridial bacterium as 900 kDa, 500 kDa and 300 kDa forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kDa complexes. The complexes (i.e. molecular weight greater than about 150 kDa) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kDa molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., Tetanus Toxin and Botulinum A and C Neurotoxins Inhibit Noradrenaline Release From Cultured Mouse Brain, J Neurochem 51(2); 522-527:1988) CGRP, substance P and glutamate (Sanchez-Prieto, J., et al., Botulinum Toxin A Blocks Glutamate Exocytosis From Guinea Pig Cerebral Cortical Synaptosomes, Eur J. Biochem 165; 675-681:1897. Thus, when adequate concentrations are used, stimulus-evoked release of most neurotransmitters is blocked by botulinum toxin. See e.g. Pearce, L. B., Pharmacologic Characterization of Botulinum Toxin For Basic Science and Medicine, Toxicon 35(9); 1373-1412 at 1393; Bigalke H., et al., Botulinum A Neurotoxin Inhibits Non-Cholinergic Synaptic Transmission in Mouse Spinal Cord Neurons in Culture, Brain Research 360; 318-324:1985; Habermann E., Inhibition by Tetanus and Botulinum A Toxin of the release of [3H]Noradrenaline and [3H]GABA From Rat Brain Homogenate, Experientia 44; 224-226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316; 244-251:1981, and; Jankovic J. et al., Therapy With Botulinum Toxin, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of 3 times $10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, Properties and use of Botulinum toxin and Other Microbial Neurotoxins in Medicine, Microbiol Rev. 56; 80-99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kDa molecular weight with a specific potency of 1-2 times $10^8$ $LD_{50}$ U/mg or greater; purified botulinum toxin type B with an approximately 156 kDa molecular weight with a specific potency of 1-2 times $10^8$ $LD_{50}$ U/mg or greater, and; purified botulinum toxin type F with an approximately 155 kDa molecular weight with a specific potency of 1-2 times $10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin (150 kDa) can also be used to prepare a pharmaceutical composition.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5 C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Because BOTOX® may be denatured by bubbling or similar violent agitation, the diluent is gently injected into the vial. For sterility reasons BOTOX® is usually administered within four hours after the vial is removed from the freezer and reconstituted. During these four hours, reconstituted BOTOX® can be stored in a refrigerator at about 2 C to about 8 C. Reconstituted, refrigerated BOTOX® has been reported to retain its potency for at least about two weeks. Neurology, 48:249-53:1997.

It has been reported that botulinum toxin type A has been used in clinical settings as follows: use of BOTOX® for intramuscular injection (multiple muscles) to treat cervical dystonia; use of BOTOX® for intramuscular injection (e.g. procerus muscle and/or corrugator supercihii muscles) to treat glabellar lines (brow furrows); use of BOTOX® to treat constipation by intrasphincter injection of the puborectalis muscle; use of BOTOX® for intramuscular injection to treat blepharospasm by injecting the lateral pre-tarsal orbicularis oculi muscle of the upper lid and the lateral pre-tarsal orbicularis oculi of the lower lid; use of BOTOX® for intramuscular injection (e.g. extraocular muscles) to treat strabismus, the amount injected varying based upon both the size of the muscle to be injected and the extent of muscle paralysis desired (i.e. amount of diopter correction desired); use of BOTOX® to treat upper limb spasticity following stroke by intramuscular injections, for example by injection into one or more of five different upper limb flexor muscles, as follows: (a) flexor digitorum profundus (e.g. 7.5 U to 30 U), (b) flexor digitorum sublimes (e.g. 7.5 U to 30 U), (c) flexor carpi ulnaris (e.g. 10 U to 40 U), (d) flexor carpi radialis (e.g. 15 U to 60 U), and (e) biceps brachii (e.g. 50 U to 200 U); use of BOTOX® to treat migraine, for example by pericranial injection symmetrically into glabellar, frontalis and temporalis muscles, or for example by injection into frontalis, corrugator, procerus, occipitalis, temporalis, trapezius and cervical paraspinal muscle groups, as a prophylactic treatment of migraine compared to vehicle as measured by decreased measures of migraine frequency, maximal severity, associated vomiting and/or acute medication use over a three month period following injection; and use of BOTOX® to treat detrusor overactivity associated with a neurological condition, for example by injection of 200 U into the detrusor muscle.

Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

The success of botulinum toxin type A to treat a variety of clinical conditions has led to interest in other botulinum toxin serotypes. Two commercially available botulinum type A preparations for use in humans include BOTOX® available from Allergan, Inc., of Irvine, Calif., and DYSPORT® available from Beaufour Ipsen, Porton Down, England. A Botulinum toxin type B preparation (MYOBLOC®) is available from Elan Pharmaceuticals of San Francisco, Calif.

SUMMARY OF THE INVENTION

The present invention meets the need of a new method for treating premature ejaculation and/or prolongation of climax time by providing a safe and effective method to a patient in need thereof.

In at least one embodiment a method for treating premature ejaculation in a patient in need thereof is provided, the method comprising the step of locally administering a Clostridial neurotoxin, such as a botulinum toxin, to the area near or at the base of the penis of the patient to thereby treat the premature ejaculation. In certain embodiments, the method of treating premature ejaculation includes local administration of a therapeutic amount of a Clostridial neurotoxin such as a botulinum toxin, by injection into the area near or at the dorsal base of the penis either alone or in combination with at least one injection into the bulbospongiosus and/or ischiocavernous muscles. In at least one further embodiment, the method of treating premature ejaculation includes the local administration of a therapeutic amount of Clostridial neurotoxin such as a botulinum toxin, by injection into the area near or at the dorsal base of the penis and into the area near or at the dorsal penile nerves. In at least one further embodiment, the method of treating premature ejaculation includes the local administration of a therapeutic amount of Clostridial neurotoxin such as a botulinum toxin by injection into the area near or at the dorsal base of the penis and into the area near or at the pudendal nerve. In at least one further embodiment, the method of treating premature ejaculation includes the local administration of a therapeutic amount of Clostridial neurotoxin such as a botulinum toxin by injection into the area near or at the dorsal base of the penis wherein the pudendal nerve is targeted. In at least one further embodiment, the method of treating premature ejaculation includes the local administration of a therapeutic amount of Clostridial neurotoxin such as a botulinum toxin, by injection into the area near or at the dorsal base of the penis, targeting the pudendal nerve, and by injection into the bulbospongiosus and/or ischiocavernosus muscles.

A preferable Clostridial neurotoxin for use in the methods herein described is a botulinum neurotoxin, which can be selected from the group consisting of botulinum neurotoxin types A, B, C, D, E, F and G, and is preferably botulinum neurotoxin type A. Various ranges/amount of botulinum neurotoxin can be therapeutically administered in accordance with the teachings of the present disclosure, for example, botulinum toxin can be administered in an amount of from about 1 unit to about 20,000 units, dependent, of course, on the potency of the botulinum toxin type utilized and its method of administration (e.g. an amount of botulinum toxin contained in a slow-release implant or pulsatile implant can be many times greater than an amount of botulinum toxin that is administered directly and at once, rather than slowly released from an implant). Exemplary useful amounts for a botulinum neurotoxin type A or type B, can be from about 1 unit to about 2500 units, or from about 10 to about 15,000 units, or from about 25 to about 1000 units respectively, or an amount or range therebetween.

DETAILED DESCRIPTION OF THE PREFERRED EMBODIMENTS

Figure 1:
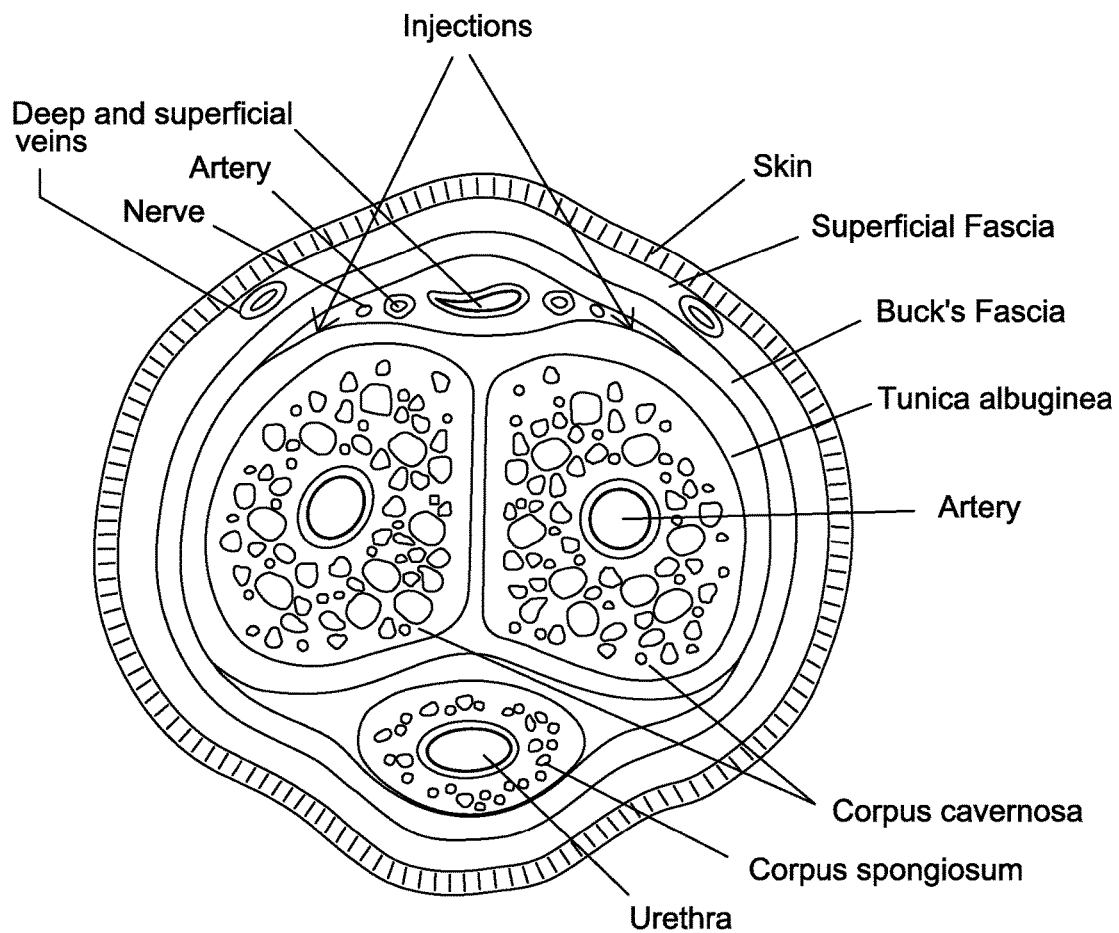
FIG. 1: Injection sites proximally at the dorsal base of the penis.

The present invention encompasses a method for treating premature ejaculation by local administration of a Clostridial toxin or its variants to a mammal, such as a human patient. Preferably, the Clostridial toxin is a botulinum toxin. In certain embodiments the botulinum toxin is a botulinum toxin type A. The botulinum toxin can be administered in an amount between about 1 unit and about 10,000 units and premature ejaculation and/or prolongation of climax time can be alleviated for between about 2 weeks and about 6 months. In particular examples, premature ejaculation and/or prolongation of climax time can be alleviated from about 2 months to about 6 months, or from about 4 to about 6 months, for example. In one aspect, the local administration step is carried out by direct administration of the Clostridial toxin, such as a botulinum neurotoxin, to at least one location of a penis of the patient.

In another embodiment, a method for treating premature ejaculation in a patient in need thereof is provided, where the method comprises a step of locally administering, by injection, a botulinum neurotoxin to the area near or at the base of the penis, thereby treating premature ejaculation in the patient. In particular embodiments, the botulinum neurotoxin is injected into at least two penile locations, and in some examples at least three penile locations. In certain embodiments, local administration of botulinum neurotoxin in the area near or at the dorsal base of the penis is into the area between the Bucks fascia and the Tunica albuginea, in proximity to the Pudendal nerve. Exemplary amounts being from about 1 to about 2500 units of a botulinum toxin type A, or any amount therebetween. When utilizing a botulinum toxin type B for example, the administered amount can be from between about 1 unit and about 25,000 units, or from about 100 units to about 20,000 units or from about 500 units to about 15,000 units or any amount therebetween.

In particular embodiments, additional administration of botulinum neurotoxin to the penis of the patient can be performed, for example from at least about 2 months to about 3 months or more after an initial administration of botulinum neurotoxin to the penis.

In particular embodiments, local administration of the botulinum neurotoxin type A is from about 1 unit to about 500 units, per injection site, per patient visit. In certain embodiments the local administration of botulinum toxin type A for treating premature ejaculation is at a dose of about 1 unit, about 2 units, about 3 units, about 4 units, about 5 units, about 6.25 units, about 10 units, about 12.5 units, about 15 units, about 20 units, about 25 units, about 30 units, about 35 units, about 37.5 units, about 40 units, about 50 units, about 55 units, about 60 units, about 65 units, about 70 units, about 75 units, about 80 units, about 85 units, about 90 units, about 95 units, about 100 units, about 105 units, about 110 units, about 115 units, about 120 units, about 125 units, about 130 units, about 135 units, about 140 units, about 145 units, about 150 units, about 155 units, about 160 units, about 165 units, about 170 units, about 175 units, about 180 units, about 185 units, about 190 units, about 195 units, or about 200 units, per injection site, per patient visit.

In particular embodiments, local administration of a botulinum neurotoxin can be to two bilateral locations on the base of the penis. In other embodiments, additional injection locations include the bulbospongiosus muscle.

Additionally, a method for prolongation of climax time in a patient in need thereof is provided wherein the method comprises the step of locally administering a botulinum neurotoxin to the base of the penis to thereby prolong the climax time in the patient. Administration of botulinum neurotoxin can be via transdermal, intramuscular, subcutaneous, subdermal, intradermal or implant administration, and can be to the dorsal base of the penis. In particular embodiments, the botulinum neurotoxin is administered by injection into the base of the penis, and the botulinum neurotoxin is botulinum neurotoxin type A or type B. In further embodiments a method for prolongation of climax time in a patient in need thereof is provided wherein the method comprises the step of locally administering a botulinum neurotoxin to the dorsal base of the penis to target the pudendal nerve, thereby prolonging the climax time in the patient.

In certain embodiments an appropriate needle for botulinum toxin injection include needles of 30-guage or smaller, preferably from about 23-gauge to about 25-gauge, and the area is preferably cleaned, such as with alcohol, before injection. Local anesthetic cream, general anesthesia, sedation or any known be useful anesthetic may be utilized, and may be necessary, depending upon the particular patient (some patients being more sensitive than others) undergoing treatment in accordance with the present methods. In particular examples, topical use of an anesthetic cream, such as, for example benzocaine, butamben, dibucaine, lidocaine, oxybuprocaine, pramoxine, proparacaine, proxymetacaine, and tetracaine can be applied before administration of the botulinum toxin via a needle.

In some instances, the dosage of botulinum neurotoxin administered can be increased until achieving the desired effect (e.g. until the patient is satisfied with the resultant delay in ejaculation). In a particular embodiment, a first dosage can be from about 10 units to about 75 units of a botulinum toxin, or from about 25 units to about 50 units of a botulinum toxin, such as BOTOX®. If unsatisfactory results are observed, treatment dosage can be increased, as determined by the medical practitioner's evaluation of the particular case at hand, the dosage, for example, being increased up to about 100 or about 200 units of a botulinum toxin. In such instances, the time between administration of increasing dosages of botulinum toxin can be about 3 weeks, preferably about 1 month and most preferably about 2 months.

The age range of patients upon which the methods herein disclosed can be practiced can be from about 18 years old to about 75 years old, more particularly, from about 18 years old to about 40 years old, and even more particularly, from about 18 years old to about 30 years old. In particular instances, the patient has tried various previous treatments that have not been found to satisfactorily treat the patient's premature ejaculation.

In some instances premature ejaculation can be experienced even after the beginning of sexual intercourse, that this, even if a patient is able to penetrate their partner (i.e. not ejaculate prior to penetration), ejaculation prematurely follows. In such instances, it is the time period between penetration and ejaculation that considered to be too short, and accordingly prolongation of climax time, here increasing the time from which sexual intercourse begins to the time of ejaculation, is desired. In particular non-limiting examples, a patient may be considered to suffer from premature ejaculation if ejaculation is achieved after from about 10 seconds to about 15 minutes after penetration, from about 15 seconds to about 10 minutes after penetration or from about 30 seconds to about 5 minutes after penetration. In particular cases, a patient may be considered to suffer from premature ejaculation if ejaculation is achieved after from about 10 seconds to about 3 minutes after penetration, from about 25 seconds to about 2 minutes after penetration or from about 30 seconds to about 1 minute after penetration.

Patients that can be treated by the methods herein disclosed may have previously partaken in regimens for treating their premature ejaculation or for prolongation of their climax time. Exemplary regiments can include taking a selective serotonin reuptake inhibitor, such as fluoxetine or paroxetine, for example. Other approaches that may have been tried include application of topical anesthetics, such as lidocaine 5% cream, applied to the penis before intercourse. Such approaches can, if desired, be combined with the methods herein disclosed in order to treat premature ejaculation or for prolongation of climax time.

In particular embodiments the botulinum neurotoxin is administered on an as-needed basis. Dosing will be determined for, and be particular to, the patient/particular presentation of premature ejaculation, with non-limiting, exemplary amounts provided herein. For example, duration of effect after botulinum administration can be up to about 4 months after administration. In particular instances, the duration of effect after botulinum administration can be from about 2 days to about 3 months after botulinum administration. Shorter duration of effects can be associated with a botulinum toxin having a short acting profile/duration of effect, such as botulinum toxin type E, relative to another botulinum toxin, such as a botulinum toxin type A, for example.

The present invention includes within its scope: (a) a botulinum neurotoxin complex as well as a pure botulinum neurotoxin obtained or processed by bacterial culturing, toxin extraction, concentration, preservation, freeze drying and/or reconstitution and; (b) modified or recombinant botulinum neurotoxin, that is botulinum neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of botulinum neurotoxins so made, and includes botulinum neurotoxins with one or more attached non-native targeting moieties for a cell surface receptor present on a cell.

Preferably, because of its clinical history to successfully treat a number of indications, a method within the scope of the present invention includes local administration of a botulinum type A or botulinum toxin type B, although botulinum toxin type B is used with a larger protein load, as compared to type A toxin. A botulinum toxin type A used in a method within the scope of the present invention can be a complex of toxin and non-toxin proteins, which together comprise a total molecular weight of up to about 900 kDa. Dosage ranges and amounts, like any pharmaceutical, are based upon size, age and health of the patient, as well as upon the particular commercial preparation of the botulinum toxin used. As known in the art, therapeutic use of botulinum toxins is tailored to the particular patient that is presented for treatment, e.g. to treat premature ejaculation. A botulinum toxin type B used in a method within the scope of the present invention can be a pure toxin or complex of toxin and non-toxin proteins, which is used at a dose of between about 50 and about 20,000 units. Other botulinum toxin serotypes may be used in proportion to the dosages and concentrations exemplified herein, according to their respective levels of biological activity. For example, most units listed in the instant disclosure are of BOTOX®, but different serotypes or strains of a botulinum toxin may be used, and different amounts may be administered. For example, about 3-4 times of DYSPORT® (a botulinum toxin type A complex available from Ipsen Inc.) than an amount of BOTOX® may be utilized; about 40-50 times of NEUROBLOC®/MYOBLOC® (a botulinum toxin type B available from Solstice Neurosciences) than an amount of BOTOX® may be utilized; and about equivalent amounts, in units, of XEOMIN® (pure botulinum toxin type A, by Merz Pharma) relative to BOTOX® units can be utilized, to achieve a desired therapeutic effect, respectively. The present invention also encompasses methods for concurrent or serial administration of a mixture of two or more of the above neurotoxins to effectively treat a patient with premature ejaculation.

Definitions

As used herein, the words or terms set forth below have the following definitions:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Active pharmaceutical ingredient" (API) means an ingredient that exerts an effect upon or after administration to a subject or patient. API's can include, for example, botulinum toxins, and the like.

"Administration", or "to administer" means the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

"Alleviating" means a reduction in the occurrence of a pain, of a headache, or of any symptom or cause of a condition or disorder. Thus, alleviating includes some reduction, significant reduction, near total reduction, and total reduction.

"Biological activity" describes the beneficial or adverse effects of a drug on living matter. When a drug is a complex chemical mixture, this activity is exerted by the substance's active ingredient but can be modified by the other constituents. Biological activity can be assessed as potency or as toxicity by an in vivo $LD_{50}$ or $ED_{50}$ assay, or through an in vitro assay such as, for example, cell-based potency assays as described in U.S. 20100203559 and U.S. 20100233802.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Climax baseline time" is the pre-treatment climax time of a patient, that is, the time or average time that it takes for a patient to climax after becoming sexually aroused.

"Climax time" or "Ejaculation time" is the time between the start of sexual intercourse (i.e. penetration of the partner) and ejaculation (i.e. when climax is achieved).

"Clostridial neurotoxin" means a neurotoxin produced from, or native to, a Clostridial bacterium, such as *Clostridium botulinum*, *Clostridium butyricum* or *Clostridium beratti*, as well as a Clostridial neurotoxin made recombinantly by a non-Clostridial species.

"Deformity" means a cosmetic, physical or functional irregularity, defect, abnormality, imperfection, malformation, depression, or distortion.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Light chain" means the light chain of a clostridial neurotoxin. It has a molecular weight of about 50 kDa, and can be referred to as the L chain, L, or as the proteolytic domain (amino acid sequence) of a botulinum neurotoxin.

"Heavy chain" means the heavy chain of a botulinum neurotoxin. It has a molecular weight of about 100 kDa and can be referred to as the H chain, or as H.

$H_C$ means a fragment (about 50 kDa) derived from the H chain of a botulinum neurotoxin which is approximately equivalent to the carboxyl end segment of the H chain, or the portion corresponding to that fragment in the intact H chain. It is believed to be immunogenic and to contain the portion of the natural or wild type botulinum neurotoxin involved in high affinity, presynaptic binding to motor neurons.

$H_N$ means a fragment (about 50 kDa) derived from the H chain of a botulinum neurotoxin which is approximately equivalent to the amino end segment of the H chain, or the portion corresponding to that fragment in the intact in the H chain. It is believed to contain the portion of the natural or wild type botulinum neurotoxin involved in the translocation of the L chain across an intracellular endosomal membrane.

$LH_N$ or $L-H_N$ means a fragment derived from a clostridial neurotoxin that contains the L chain, or a functional fragment thereof coupled to the $H_N$ domain It can be obtained from the intact clostridial neurotoxin by proteolysis, so as to remove or to modify the $H_C$ domain.

"Implant" means a controlled release (e.g., pulsatile or continuous) composition or drug delivery system. The implant can be, for example, injected, inserted or implanted into a human body.

"Local administration" means direct administration of a pharmaceutical at or to the vicinity of a site on or within an animal body, at which site a biological effect of the pharmaceutical is desired, such as via, for example, intramuscular injection, intra-dermal injection, subdermal injection, subcutaneous injection, placement of an implant for administration of the neurotoxin, or topical administration. Local administration excludes systemic routes of administration, such as intravenous or oral administration. Topical administration is a type of local administration in which a pharmaceutical agent is applied to a patient's skin.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Neurotoxin" includes Clostridial neurotoxins both as pure toxin and complexed with one to more non-toxin, toxin associated proteins, whether made by the native Clostridial bacterium or by recombinant means in a non-Clostridial species. "Botulinum neurotoxin" means non-complexed botulinum neurotoxin (i.e. pure botulinum neurotoxin molecule having a molecular weight of about 150 kDa) or as a complex (i.e. having a molecular weight of about 300 to about 900 kDa weight complex comprising a neurotoxin molecule and one or more associated non-toxic molecules), and excludes botulinum toxins which are not neurotoxins such as the cytotoxic botulinum toxins C2 and C3, but can include recombinantly made, hybrid, modified, and chimeric botulinum toxins.

"Patient" means a human subject receiving medical care from a physician.

"Peripherally administering" or "peripheral administration" means subdermal, intradermal, transdermal, or subcutaneous administration, but excludes intramuscular administration. "Peripheral" means in a subdermal location, and excludes visceral sites.

"Pharmaceutical composition" means a composition comprising an active pharmaceutical ingredient, such as, for example, a botulinum toxin, and at least one additional ingredient, such as, for example, a stabilizer or excipient or the like. A pharmaceutical composition is therefore a formulation which is suitable for diagnostic or therapeutic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

"Prolongation of climax time" means an increase in time (increase in climax baseline time) from which a patient becomes sexually aroused to the time of sexual climax (i.e. orgasm). In one aspect, "treating premature ejaculation" means increasing the time between the beginning of sexual arousal of a patient and ejaculation by the patient; and in particular instances, it can mean increasing the time from which sexual intercourse begins to the time of ejaculation.

"Therapeutic formulation" means a formulation can be used to treat and thereby alleviate a disorder or a disease, such as, for example, premature ejaculation.

"Therapeutically effective amount," as used herein, means an amount of a Clostridial neurotoxin, for example a botulinum toxin type A, B, C, D, E, F and G, that ameliorates, or eliminates one or more symptoms of a particular disease or condition such as premature ejaculation.

"Topical administration" excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Treating" means to alleviate (or to eliminate) at least one symptom, either temporarily or permanently. Here, this includes increasing the time (i.e. prolongation of climax time) it takes a patient to reach climax after sexual arousal. In a particular example, climax time is the time between the start of intercourse and the time at which climax is achieved.

"Variant" means a clostridial neurotoxin, such as wild-type botulinum toxin serotype A, B, C, D, E, F or G, that has been modified by the replacement, modification, addition or deletion of at least one amino acid relative to wild-type botulinum toxin, which is recognized by a target cell, internalized by the target cell, and catalytically cleaves a SNARE (SNAP (Soluble NSF Attachment Protein) Receptor) protein in the target cell.

An example of a variant neurotoxin component can comprise a variant light chain of a botulinum toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a botulinum toxin type A having an amino acid sequence removed may have a shorter biological persistence than that of the parent (or native) botulinum toxin type A light chain.

"Vehicle" or "reconstitution vehicle" means a liquid composition that can be used to reconstitute a solid botulinum formulation into a liquid botulinum pharmaceutical composition.

"Wild type neuronal binding moiety" means that portion of a neurotoxin which is native to the neurotoxin and which exhibits a specific binding affinity for a receptor on a neuron. Thus, wild type or native neuronal binding moiety excludes a binding moiety with is not native to the neurotoxin.

Methods of Treatment

In at least one embodiment, a method of treating premature ejaculation is provided wherein a therapeutic amount of Clostridial neurotoxin such as a botulinum toxin is injected locally: (i) proximally at the dorsal base of the penis (similar to penile nerve block approach); and (ii) additional pelviperianal administration into the bulbospongiosus muscle.

In at least one embodiment, a method of treating premature ejaculation is provided wherein injection of a therapeutic amount of Clostridial neurotoxin such as a botulinum toxin is used to block the nerve pathways through the pudendal nerve. In this method, reduced sensory signaling can reduce the trigger of the ejaculatory reflex, and as ejaculation is a spinal cord reflex, inhibiting the stereotyped rhythmic contractions of these muscles with the injection of a Clostridial neurotoxin such as a botulinum toxin, can have a beneficial effect in treating premature ejaculation.

The penis is innervated by the pudendal nerve and cavernous nerves. The pudendal nerve eventually divides into the right and left dorsal nerves of the penis that pass under the pubis symphysis to travel just below the Buck fascia close to the arteries. The pudendal nerves supply somatic motor and sensory innervation to the penis. The cavernous nerves are a combination of parasympathetic and visceral afferent fibers and provide the nerve supply to the erectile tissue. The cavernous nerves run in the crus and corpora of the penis, primarily dorsomedial to the deep penile arteries.

In at least one embodiment a method of treating premature ejaculation by local administration of a botulinum toxin is provided wherein the right and left dorsal penile nerves are blocked proximally to the base of the penis.

In exemplary embodiments, the area that is to receive the botulinum neurotoxin administration is first cleaned utilizing alcohol, such as by utilizing an alcohol wipe, for example. Local anesthetic (as disclosed herein) is then applied to the cleaned area. The anesthetic can be applied topically with local sterile single use local anesthetic (LA) gel or cream (eg, lidocaine gel, cream) and, when ready the injection sites can be sterilized.

An appropriate sized needle (e.g. 22-25 gauge) should be used for injection into the penis.

In at least one embodiment a method of treating premature ejaculation by local administration of a botulinum toxin is provided wherein the botulinum toxin is injected bilaterally through the fascia into the pear shaped spaces on each side of the suspensory ligament. This avoids mid-line injection and therefore potential damage to the dorsal vessels and provides increased chance of diffusion into the nerves to block them. The membranous layer of superficial fascia and the suspensory ligament suspended from the symphysis pubis of the penis, fuses with the deep penile (Buck's) fascia (under which pass the dorsal nerves, arteries and veins, and the penile muscle fibers part of Tunica Albuginea are located). Injection of botulinum toxin is made bilaterally on either side of the midline, avoiding injecting into the superficial dorsal penile vein (see FIG. 1). The site of insertion of the needle is shown passing through the membranous layer of the superficial fascia and then through the thicker Bucks fascia. The needle can be directed to a depth of about 0.5 cm or until loss of resistance is felt to suggest that the tip of the needle is within the Buck fascia. For each injection site a test aspiration can be done to ensure that there was no accidental puncture of an artery, vein or the corpus cavernosum or corpus spongiosum. In certain embodiments, for each local administration, the dose of botulinum toxin is slowly injected to infiltrate the area of the penile nerve and smooth muscle fibers of the Bulbospongiosus part of tunica albuginea.

Figure 2:
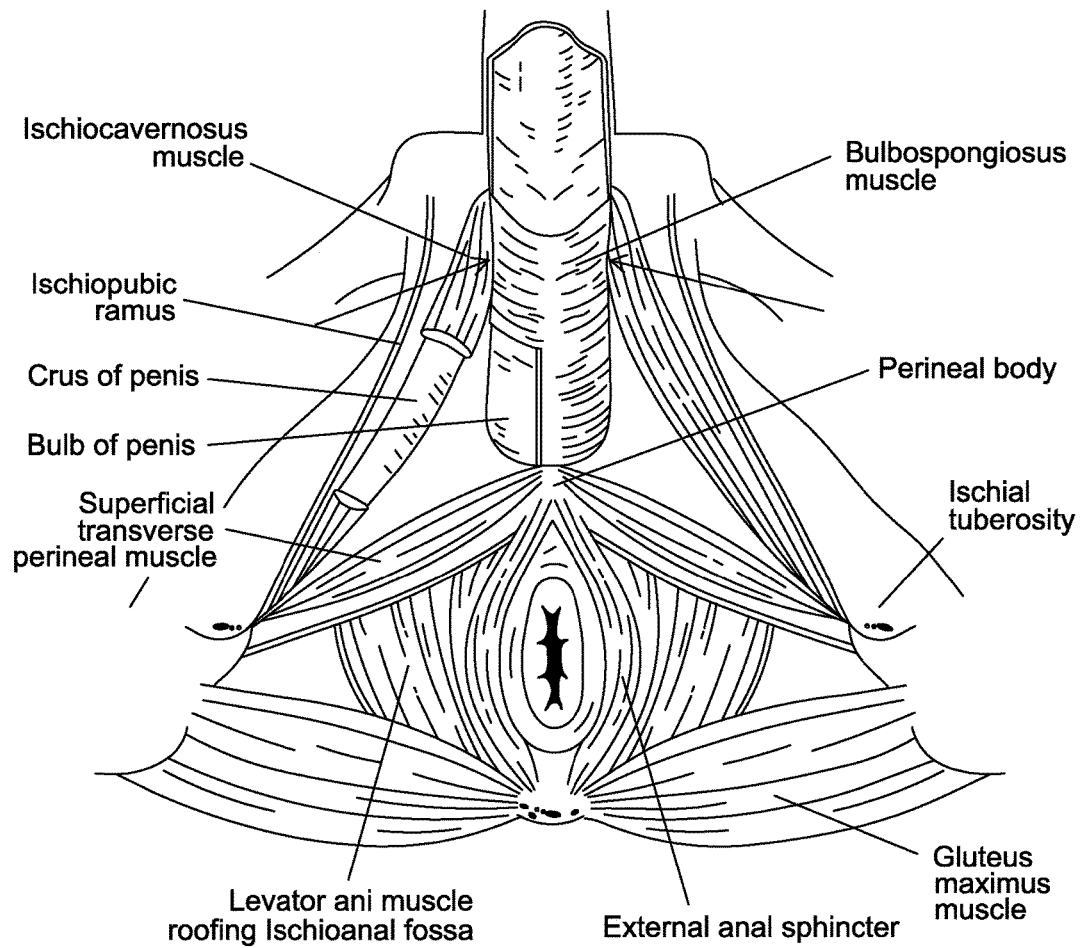
FIG. 2: Injection sites at the perineum and the base of the penis into the bulbospongiosus muscles.

In at least one embodiment a method of treating premature ejaculation by local administration of a botulinum toxin is provided wherein the botulinum toxin is injected at sites at the perineum and the base of the penis into the bulbospongiosus muscles. Before injection, the scrotum is lifted up to provide an opportunity to identify the base of the penis in the area above the anus and the transverse line across in front of the ischial tuberosities at the sides. The injection is made close to the scrotal base to avoid the anal sphincter muscle. The injection sites can first be aneasthesized topically with local sterile single use local anesthetic (LA) gel or cream (eg, lidocaine gel or cream) applied gently topically and, when ready the injection sites can be sterilized. An appropriate sized needle (e.g. 22-25 gauge) can be used for injection into the penis. Injection is made bilaterally on either side of the midline of the penile basis. The site of insertion of the needle is shown passing through the membranous layer of the deep fascia which covers the nerves and muscles of the perineum (pudendus nerve, ischiocavernous and bulbospongiosus muscles) (see blue lines in FIG. 2). For each injection site a test aspiration can be done to ensure that there was no accidental puncture of an artery, vein or the corpus cavernosum or corpus spongiosum. In certain embodiments, for each local administration, the dose of botulinum toxin is slowly injected to infiltrate the area of the penile nerve and smooth muscle fibers of the Bulbospongiosus.

In certain embodiments the patient is observed for at least 60 minutes post-injection. Prior to leaving the site, patients can be checked to see if they experience any adverse events post-treatment.

In certain embodiments, post-procedurally, the patient is instructed not to engage in sexual activity for the following 48 hours, and if edema and/or inflammation is observed, a cold compress or ice pack may be applied. Typically, patients observe effects (e.g. delaying of previously premature ejaculation) within about 48 to about 72 hours, with full results (maximum delay) usually observed after about 3 weeks. The following are non-limiting examples where patient's suffering from premature ejaculation are treated.

EXAMPLES

The following examples illustrate embodiments and aspects of the present invention and are not intended to limit the scope of the present invention.

Example 1

Treatment of premature ejaculation in three cohorts with escalating doses of either a total dose of 25 U or a total dose of 50 U of botulinum toxin type A (BOTOX).

The dilution for the first 25 U total dose cohort is a vial of BOTOX 100 U diluted in 4 mL with 0.9% non-preserved sterile saline i.e. with a final diluted concentration of 25 U/mL. (a) For the 25 U total dose cohort, the patient with the first injection regimen (1) will be injected with 0.5 mL of the diluted BOTOX on each side of the midline into the dorsal base of the penis (i.e. 12.5 U per injection site) and a total injection volume of 1 mL (total dose of 25 U divided in 2 injection sites); (b) For the 25 U total dose cohort the patients with the second injection regimen (2) will be injected both according to regimen (1) but only with 0.25 mL of the diluted BOTOX on each side into the proximal dorsal base of the penis (i.e. 6.25 U per injection site), as well as 0.25 mL of the diluted BOTOX on each side of the midline into the bulbuspongiosus muscles of the perineum (i.e. 6.25 U per injection site) and a total injection volume of 1 mL (total dose of 25 U divided in 4 injection sites).

The dilution for the 50 U dose cohort is a vial of 100 U diluted in 2 mL with 0.9% non-preserved sterile saline i.e. with a final diluted concentration of 50 U/mL. (a) For the 50 U total dose cohort the patients with the first injection regimen (1) will be injected with 0.5 mL of the diluted BOTOX on each side of the midline into the dorsal base of the penis (i.e. 25 U per injection site) and a total injection volume of 1 mL (total dose of 50 U divided in 2 injection sites); (b) For the 50 U total dose cohort the patients with the second injection regimen (2) will be injected both according to regimen (1) but only with 0.25 mL of the diluted BOTOX on each side into the proximal dorsal base of the penis (i.e. 12.5 U per injection site), as well as 0.25 mL of the diluted BOTOX on each side of the midline into the bulbuspongiosus muscles of the perineum (12.5 U per injection site) and a total injection volume of 1 mL (total dose of 50 U divided in 4 injection sites).

The dilution for the 100 U dose cohort is a vial of 100 U diluted in 1 mL with 0.9% non-preserved sterile saline i.e. with a final diluted concentration of 100 U/mL. (a) For the 100 U total dose cohort the patients with the first injection regimen (1) will be injected with 0.5 mL of the diluted BOTOX on each side of the midline into the dorsal base of the penis (i.e. 50 U per injection site) and a total injection volume of 1 mL (total dose of 100 U divided in 2 injection sites); (b) For the 100 U total dose cohort the patients with the second injection regimen (2) will be injected both according to regimen (1) but only with 0.25 mL of the diluted BOTOX on each side into the proximal dorsal base of the penis (i.e. 25 U per injection site), as well as 0.25 mL of the diluted BOTOX on each side of the midline into the bulbuspongiosus muscles of the perineum (25 U per injection site) and a total injection volume of 1 mL (total dose of 100 U divided in 4 injection sites).

Example 2

Treatment of Premature Ejaculation

A male patient is diagnosed with premature ejaculation after presenting with climax times of less than 15 seconds after beginning sexual intercourse. The patient is treated with an effective amount of a botulinum toxin, BOTOX®.

The doctor prepares the patient for injection by cleaning the patient's penis at the dorsal base with a skin disinfecting agent and subsequently applies topical lidocaine anesthesia cream or a local injection of lidocaine to anesthetize the area.

Treatment consists of two injections (bilaterally) on both sides of the midline at the dorsal base of the penis. The injections are through the Superficial Fascia, into the area between the Bucks Fascia and the Tunica Albuginea, and in the proximity of the Pudendal nerve. The Pudendal nerve is targeted.

25 units of BOTOX® is injected at each injection site utilizing a 25 gauge needle for each injection, for a total of 50 units.

Post procedure, the patient is instructed not to have sex during the following 48 hours. If edema and/or inflammation is noted, appropriate application of an ice-pack to the area is recommended (applied not longer than about 15 minutes at a time).

At a follow up session 2 weeks later, the patient reports a doubling in his climax baseline time, with on some occasions lasting for about 10 to 15 minutes, and that both he and his partner are very satisfied with the resultant outcome of the treatment.

What is claimed is:

1. A method for treating premature ejaculation in a patient, the method comprising the step of locally administering a therapeutically effective amount of botulinum toxin to a pudendal nerve near or at the base of the penis of the patient, thereby treating the premature ejaculation of the patient.

2. The method of claim 1, wherein between about 5 and about 200 units of botulinum toxin is administered.

3. The method of claim 1, wherein the botulinum toxin is administered by injection to the dorsal base of the penis.

4. The method of claim 3, wherein the botulinum toxin is administered by at least two injections performed bilaterally on both sides of the midline of the dorsal base of the penis.

5. The method of claim 4, wherein the botulinum toxin is administered into the area between the Bucks fascia and the Tunica albuginea, in proximity to the pudendal nerve.

6. The method of claim 5, further comprising administering the botulinum toxin to the bulbospongiosus muscle.

7. The method of claim 1, wherein the botulinum toxin is administered topically.

8. The method of claim 1, further comprising administering the botulinum toxin to the bulbospongiosus muscle.

\* \* \* \* \*

UNITED STATES PATENT AND TRADEMARK OFFICE
CERTIFICATE OF CORRECTION

PATENT NO. : 9,764,010 B2
APPLICATION NO. : 13/971542
DATED : September 19, 2017
INVENTOR(S) : Anders N. Nilsson Neijber et al.

It is certified that error appears in the above-identified patent and that said Letters Patent is hereby corrected as shown below:

On the Title Page

In item (56), in Column 2, under "Other Publications", Line 2, delete "curtosey" and insert -- courtesy --, therefor.

In item (56), in Column 2, under "Other Publications", Line 4, delete "("Bloc penien chex l'adulte:" and insert -- ("Bloc penien chez l'adulte: --, therefor.

In item (56), in Column 2, under "Other Publications", Line 21, delete "preipheral" and insert -- peripheral --, therefor.

In the Specification

In Column 2, Line 36, delete "phosphodiestrase" and insert -- phosphodiesterase --, therefor.

In Column 2, Lines 53-54, delete "lidocaine-prilocalne" and insert -- lidocaine-prilocaine --, therefor.

In Column 3, Line 41, after "vials)" insert -- . --.

In Column 5, Line 4, delete "hemaglutinin" and insert -- hemagglutinin --, therefor.

In Column 5, Line 5, delete "nonhemaglutinin" and insert -- nonhemagglutinin --, therefor.

In Column 6, Line 56, delete "-5 C." and insert -- -5 °C. --, therefor.

In Column 7, Line 5, delete "2 C." and insert -- 2 °C. --, therefor.

In Column 7, Line 5, delete "8 C." and insert -- 8 °C. --, therefor.

In Column 7, Line 13, delete "corrugator supercihii" and insert -- corrugator supercilii --, therefor.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,764,010 B2

In Column 8, Line 9, delete "ischiocavernous" and insert -- ischiocavernosus --, therefor.

In Column 10, Line 7, delete "30-guage" and insert -- 30-gauge --, therefor.

In Column 13, Line 4, delete "Clostridium beratti," and insert -- Clostridium baratii, --, therefor.

In Column 13, Line 9, delete "free" and insert -- free" --, therefor.

In Column 14, Line 17, delete "aspargine," and insert -- asparagine, --, therefor.

In Column 16, Line 61, delete "aneasthesized" and insert -- anesthetized --, therefor.

In Column 17, Line 3, delete "ischiocavernous" and insert -- ischiocavernosus --, therefor.

In Column 17, Line 51, delete "bulbuspongiosus" and insert -- bulbospongiosus --, therefor.

In Columns 17-18, Line 67 (Column 17) and Line 1 (Column 18), delete "bulbuspongiosus" and insert -- bulbospongiosus --, therefor.

In Column 18, Line 18, delete "bulbuspongiosus" and insert -- bulbospongiosus --, therefor.